United States Patent [19]

Edwards

[11] Patent Number: 4,499,098
[45] Date of Patent: Feb. 12, 1985

[54] INSECTICIDAL N-CARBAMOYL-OXADIAZOLIDIN-5-ONES AND THIONES

[75] Inventor: Laroy H. Edwards, Napa, Calif.

[73] Assignee: Chevron Research Company, San Francisco, Calif.

[21] Appl. No.: 514,073

[22] Filed: Jul. 15, 1983

[51] Int. Cl.³ .................... A01N 43/82; C07D 273/02
[52] U.S. Cl. ....................................... 514/364; 548/144
[58] Field of Search ........................ 548/144; 424/269

[56] References Cited

U.S. PATENT DOCUMENTS 3,337,575  8/1967  Boesch et al. .................. 548/144
4,426,379  1/1984  Edward .......................... 424/200

FOREIGN PATENT DOCUMENTS 1057995  2/1967  United Kingdom ............... 548/144

Primary Examiner—Paul M. Coughlan, Jr.
Assistant Examiner—Cecilia Shen
Attorney, Agent, or Firm—S. R. LaPaglia; T. G. DeJonghe; S. L. Biggs

[57] ABSTRACT

Compounds of the formula:

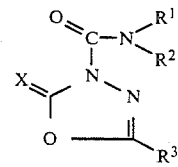

wherein X is oxygen or sulfur; $R^1$ and $R^2$ are independently lower alkyl having from 1 to 4 carbon atoms; and $R^3$ is lower alkyl having from 1 to 6 carbon atoms, lower cycloalkyl having from 3 to 6 carbon atoms optionally substituted with methyl or ethyl, lower alkoxyalkyl having up to a total of 8 carbon atoms or lower alkylthioalkyl having up to a total of 8 carbon atoms are insecticidal.

19 Claims, No Drawings

INSECTICIDAL N-CARBAMOYL-OXADIAZOLIDIN-5-ONES AND THIONES

BACKGROUND OF THE INVENTION

The present invention relates to novel N-carbamoyl-oxadiazolidin-5-ones and thiones which are active as insecticides.

The cyclization of thio- and dithiocarbazic acid ester derivatives which are acylated in position 3 by the radical of a carboxylic, sulfonic, carbamic, phosphoric, thiophosphoric or thiophosphonic acid with phosgene to give compounds of the formula:

[structure: Acyl-N—N ring with O= and S—yR substituents]

where y is O or S, Acyl is $-COC_6H_5$, $-SO_2C_6H_5$, $CO_2C_2H_5$, $CON(CH_3)_2$ or $-\overset{X}{\underset{R''}{\overset{\|}{P}}}\!\!-\!OR'$, is disclosed by Rufenacht in Helvetica Chimica Acta 56, 162-175 (1973). The compounds where Acyl is phosphoryl or thiophosphoryl $$\left(-\overset{X}{\underset{R''}{\overset{\|}{P}}}\!\!-\!OR'\right)$$

are disclosed as having an "insecticidal, acaricidal, and nematicidal effect"; however, the compounds where X is O are disclosed as unstable.

Rufenacht, supra, also discloses the preparation of compounds of the formulae:

[structures (A) and (B)]

The compounds of formula (B) are disclosed as "having an insecticidal and acaricidal effect" but also as "not stable enough under the conditions of practical pesticide use".

U.S. Pat. No. 3,661,926 issued to Van den Bos et al. discloses 2-oxo-3-dialkoxyphosphoro-5-alkyl (or cycloalkyl of 5 to 7 carbons)-1,3,4-oxadiazolines as insecticidal.

U.S. Pat. No. 3,523,951 issued to Rufenacht teaches derivatives of 1,3,4-thiadiazole as possessing insecticidal activity.

My commonly assigned patent application, "Insecticidal 2-Oxo-3-Dialkoxyphosphoro-5-Cyclopropyl-1,3,4-Oxadiazoline," Ser. No. 343,088, filed Jan. 27, 1982 now U.S. Pat. No. 4,426,379, discloses compounds of the formula:

[structure with P(OR¹)(OR²)=Y, N—N, R, O, =O]

wherein R is hydrogen, lower alkyl or lower alkoxy; $R^1$ and $R^2$ are independently lower alkyl; and Y is either oxygen or sulfur.

My commonly assigned U.S. patent application, "Insecticidal 5-Thiocarbamoyl-1,3,4-Oxadiazoles", Ser. No. 514,067, filed July 15, 1983, discloses insecticidal compounds of the formula:

[structure with R³, O, N—N ring, SCN(R¹)(R²), O]

wherein $R^1$ and $R^2$ are independently lower alkyl having from 1 to 4 carbon atoms; and $R^3$ is lower alkyl having 1 to 6 carbon atoms, lower cycloalkyl having 3 to 6 carbon atoms optionally substituted with methyl or ethyl, lower alkoxyalkyl having up to a total of 8 carbon atoms or lower alkylthioalkyl having up to a total of 8 carbon atoms.

SUMMARY OF THE INVENTION

The present invention relates to insecticidal N-carbamoyl-oxadiazolidin-5-ones and thiones of the formula:

$$\text{[structure I]} \tag{I}$$

wherein X is oxygen or sulfur; $R^1$ and $R^2$ are independently lower alkyl having from 1 to 4 carbon atoms; and $R^3$ is lower alkyl having from 1 to 6 carbon atoms, lower cycloalkyl having from 3 to 6 carbon atoms optionally substituted with methyl or ethyl, lower alkoxyalkyl having up to a total of 8 carbon atoms or lower alkylthioalkyl having up to a total of 8 carbon atoms.

Among other factors, the present invention is based on my surprising finding that the compounds of this invention are effective insecticides, and are particularly effective against certain economically important pests such as aphids.

Preferred compounds include those which have $R^3$ groups in which the carbon atom attached to the oxadiazolidine ring is a tertiary carbon.

Definitions

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group —$(CH_2)_m$— wherein m is an integer greater than zero. Typical alkylene groups include methylene, ethylene, propylene, and the like.

The term "alkoxy" refers to the group —OR′ wherein R′ is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkyl" refers to an alkyl group substituted with an alkoxy group. The term "lower alkoxyalkyl" refers to groups having up to a total of 8 carbon atoms and includes, for example, ethoxymethyl, methoxymethyl, 2-methoxypropyl, and the like.

The term "alkylthio" refers to the group —SR′ wherein R′ is an alkyl group. The term "lower alkylthio" refers to alkylthio groups having from 1 to 6 carbon atoms; examples include methylthio, ethylthio, n-hexylthio, n-propylthio, isopropylthio, isobutylthio, and the like.

The term "alkylthioalkyl" refers to an alkyl group substituted with an alkylthio group. The term "lower alkylthioalkyl" refers to groups having up to a total of 8 carbon atoms and includes, for example, ethylthiomethyl, methylthiomethyl, 2-methylthiopropyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "tertiary carbon" refers to the group

wherein R′, R‴ and R⁗ are independently lower alkyl, or R‴ is an alkoxy or alkylthio group, or R‴ and R⁗ taken together are an alkylene group, thus forming a cycloalkyl group.

The term "oxadiazolidine" refers to the

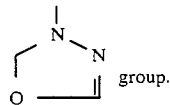 group.

The conventional numbering system for this group is shown below:

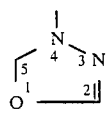

DETAILED DESCRIPTION OF THE INVENTION (a) The compounds of the present invention where X is oxygen may be prepared according to the following reaction scheme:

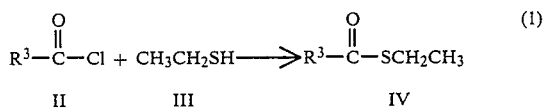

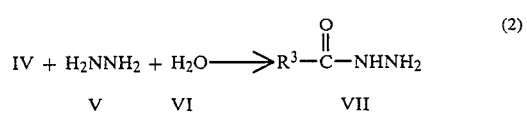

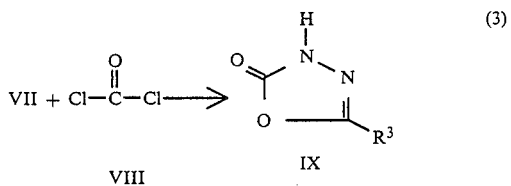

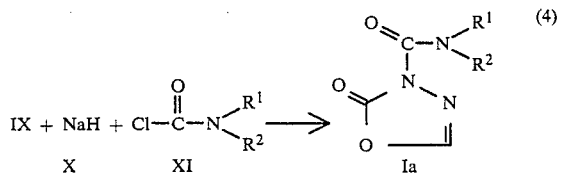

wherein $R^1$, $R^2$ and $R^3$ are as previously defined in conjunction with formula I.

Reaction (1) is conducted by combining approximately equimolar amounts of the acid chloride II and thiol III. The acid chloride II is prepared from the corresponding carboxylic acid by techniques well known to the art, such as treatment with thionyl chloride. Although the reactants may be combined in any order, it is preferred to add III to II. The reaction is conducted at a temperature from about 0° C. to about 50° C., preferably from about 0° C. to about 25° C., and is generally complete within about 8 to about 12 hours. The product, IV, is isolated by conventional procedures such as extraction, stripping, chromatography, distillation, and the like.

Reaction (2) is conducted by combining IV in solvent, V, and VI. Although approximately equimolar amounts of IV and V may be used, in excess of V relative to IV may be used. Suitable solvents include protic solvents such as methanol, ethanol, other low molecular weight alcohols, water, and the like. If desired, a hydrazine hydrate, such as hydrazine monohydrate, may be used instead of anhydrous hydrazine, V and water, VI. It is preferred to drop a mixture of IV in solvent into a stirred solution of V and VI. The reaction is conducted at a temperature from about 0° C. to about 50° C., preferably from about 0° C. to about 25° C., and is generally complete within about 6 to about 8 hours. It may be desirable to cool the reaction mixture during the addition, maintaining the temperature at about 0° C. to about 5° C. The product, VII, is isolated by conventional procedures such as extraction, drying, stripping, filtration, crystallization, distillation, and the like.

Reaction (3) is conducted by combining approximately equimolar amounts of VII and VIII in solvent. The reaction is conducted at a temperature from about 0° C. to about 50° C., preferably about 0° C. to about 25° C., and is generally complete within about 8 to about 12 hours. It is preferred to add VIII slowly to a stirred mixture of VII in solvent. It is preferred to cool the reaction system during the addition, maintaining the temperature in the range of about 0° C. to about 15° C.

Suitable solvents include inert organic solvents such as methylene chloride, ethyl acetate, toluene, and the like. The product, IX, is isolated by conventional procedures such as stripping, washing, extraction, filtration, drying, crystallization, distillation, and the like.

Reaction (4) is conducted by first combining approximately equimolar amounts of IX and X in solvent. The addition is conducted at a temperature from about 0° C. to about 50° C., preferably from about 0° C. to about 25° C., or, for convenience, at ambient temperature. After the addition is complete, the reaction mixture is stirred from about 6 to about 8 hours and/or refluxed about 2 to about 3 hours. Then, XI is slowly added to the reaction mixture. This addition is conducted at a temperature from about 0° C. to about 25° C., preferably from about 0° C. to about 5° C. Then, the reaction mixture may be allowed to come to ambient temperature. The reaction is conducted at a temperature from about 25° C. to about 65° C., preferably from about 25° C. to about 50° C., and is generally complete within about 3 to about 6 hours. Suitable solvents include organic solvents such as dimethoxyethane, tetrahydrofuran, and the like. The product, Ia, is isolated by conventional procedures such as washing, extraction, drying, stripping, chromatography, distillation, and the like.

Reaction (4) may also be conducted using phosgene and the appropriate dialkylamine ($HNR^1R^2$) replacing XI.

(b) The compounds of this invention where X is sulfur are conveniently prepared by starting with the appropriate reagent II, following Reactions (1) and (2), and then proceeding according to the following synthetic scheme:

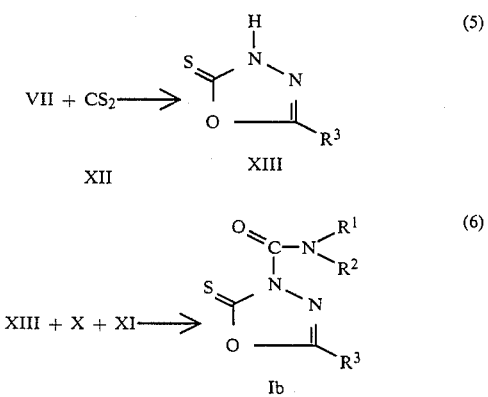

wherein $R^1$, $R^2$ and $R^3$ are as previously defined.

Reaction (5) is conducted by combining VII and XII in solvent. It is preferred to use an excess of XII relative to VII, on the order of from about 1 to 2 equivalents XII per equivalent VII due to the volatility of the carbon disulfide. It is preferred to add XII to a stirred mixture of VII in solvent. Suitable solvents include polar organic solvents such as dimethylformamide, dimethylsulfoxide, and the like. The reaction is conducted at a temperature from about 0° C. to about 50° C., preferably from about 0° C. to about 25° C., and is generally complete within about 8 to about 12 hours. The product, XIII, is isolated by conventional procedures such as filtration, stripping, extraction, and the like.

Intermediate XIII is then converted to product Ib according to Reaction (6) which is conducted in the same manner as Reaction (4).

Utility

The compounds of this invention are useful for controlling insects, particularly insects such as aphids. However, some insecticidal compounds of this invention may be more insecticidally active than others against particular pests.

Like most insecticides, they are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from 5–80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing or emulsifying agents used in insecticidal formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1–15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersants, and may consist entirely of the toxicant with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for insecticidal applications include simple solutions of the active ingredient in a dispersant in which it is completely soluble at the desired concentration such as acetone, alkylated naphthalenes, xylene, or other organic solvents. Granular formulations, wherein the toxicant is carried on relatively coarse particles, are of particular utility for aerial distribution or for penetration of cover-crop canopy. Baits, prepared by mixing solid or liquid concentrates of the toxicant with a suitable food such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier such as the Freons, may also be used. All of these techniques for formulating and applying the active ingredient are well known in the art.

The percentages by weight of the toxicant may vary according to the manner in which the composition is to be applied and the particular type of formulation, but in general comprise 0.1–95% of the toxicant by weight of the insecticidal composition.

The insecticidal compositions may be formulated and applied with other active ingredients, including nematocides, insecticides, fungicides, bactericides, plant-growth regulators, fertilizers, etc. In applying the chemical, an effective amount and concentration of the toxicant of this invention is, of course, employed.

The terms "insecticide" and "insect" as used herein refer to their broad and commonly understood usage rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms, and the like.

A further understanding of the invention can be had in the following non-limiting Examples. Wherein, unless expressly stated to the contrary, all temperatures and temperature ranges refer to the Centigrade system and the term "ambient" or "room temperature" refers to about 20°–25° C. The term "percent" refers to weight percent and the term "mol" or "mols" refers to gram mols. The term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of

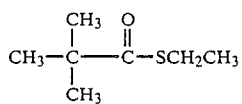

Ethyl Trimethylacetylthioate

Trimethylacetyl chloride, 100 g (0.83 mole), was stirred at 0° C. Then 51.5 g (0.83 mole) ethylthiol was added and stirring was continued until the mixture returned to room temperature. The reaction mixture was then heated a total of 10 hours until no more HCl evolved. The mixture was evacuated to remove any HCl; the above-identified product was then used in Example 2 without further isolation.

EXAMPLE 2

Preparation of

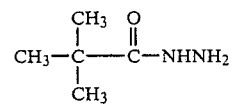

Trimethylacetyl Hydrazide

A mixture of 101.5 g (0.7 mole) of ethyl trimethylacetylthioate (the product of Example 1) in 75 ml methanol was stirred. This methanol mixture was added dropwise to a stirred solution of 24.5 g (0.7 mole) hydrazine in 120 ml water. The reaction mixture was stirred over the weekend. Stripping of the solvent gave 78.1 g of the above-identified product.

EXAMPLE 3

Preparation of

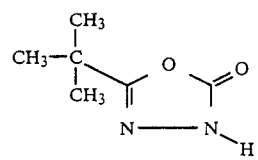

2-Tert-Butyl-1,3,4-$\Delta^2$-Oxadiazolidin-5-one

In a flask equipped with a thermometer, dropping funnel and mechanical stirrer, 147.8 g (0.186 mole) phosgene (about 12.5% in benzene) was placed. The reaction vessel was cooled to 15° C.; then 20 g (0.166 mole) trimethylacetyl hydrazide (the product of Example 2) in ethyl acetate (about 100 ml) was dropped in. The reaction mixture was stirred overnight. The reaction mixture was washed with a dilute sodium bicarbonate solution and then extracted with methylene chloride. The organic phase was dried and stripped to give the above-identified product.

EXAMPLE 4

Preparation of

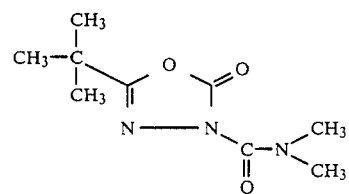

2-Tert-Butyl-4-Dimethylcarbamoyl-1,3,4-$\Delta^2$-Oxadiazolidin-5-one

To a stirred mixture of 10.5 g (0.074 mole) 2-tert-butyl-1,3,4-$\Delta^2$-oxadiazolidin-5-one (the product of Example 3) in 100 ml dimethoxyethane, 24.0 g of 60% sodium hydride (0.074 mole) were added slowly. After the sodium hydride reaction appeared complete, 8.0 g (0.074 mole) N,N-dimethylcarbamoyl chloride were added. The reaction mixture was refluxed 3 hours. The mixture was then washed with water and extracted with methylene chloride. The organic phase was then dried, stripped and chromatographed on silica gel, eluting with ether, to give the above-identified product as a white solid, melting point 71°-73° C.

Elemental analysis for C₉H₁₅N₃O₃ showed: calculated %C 50.69%, %H 7.09, and %N 19.71; found %C 50.89, %H 7.24, and %N 20.11.

EXAMPLE 5

Preparation of

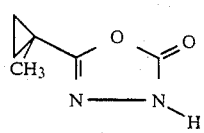

2-(1-Methylcyclopropyl)-1,3,4-Δ²-Oxadiazolidin-5-one (a) A stirred mixture of 100 g (1 mole)

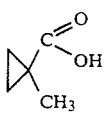

1-methylcyclopropane carboxylic acid and 150 ml ethyl ether was cooled to 5° C.; then 119 g (1 mole) thionyl chloride was added dropwise. The resulting mixture was refluxed 8 hours. The reaction mixture was cooled to 5° C.; then 62 g (1 mole) ethylthiol was added. The resulting mixture was refluxed 6 hours and then stirred over the weekend. The solvent was stripped and the product (residue) used in Step (b) without further isolation.

(b) A stirred mixture of 48 g (1.5 mole) hydrazine and 12 ml water was cooled to 5° C.; the product of Step (a) in 80 ml methanol was dropped into that mixture. The resulting mixture was stirred overnight and then stripped. Methylene chloride (about 300 ml) was added to the residue. The methylene chloride mixture was dried and stripped to give 85 g of a dark oil which crystallized upon cooling. The product, 1-methylcyclopropane carboxylic acid hydrazide, was used in Step (c) without further isolation.

(c) The crystals obtained in Step (b) were placed in a 2-liter, three-neck, round-bottom flask. Methylene chloride (about 150 ml) was added and the resulting mixture stirred until the crystals dissolved. The methylene chloride solution was cooled to 5° C.; then 590.5 g of 12.5% phosgene (0.75 mole) were dropped in. The resulting mixture was refluxed 7 hours and then stripped to give the above-identified product as a crystalline solid. The residue was washed with petroleum ether and filtered. The product was obtained as 66.6 g of light brown crystals, melting point 68°-70° C.

Elemental analysis for C₆H₈N₂O₂ showed: calculated %C 51.36%, %H 5.75, and %N 20.08; found %C 51.96, %H 6.01, and %N 21.52.

EXAMPLE 6

Preparation of

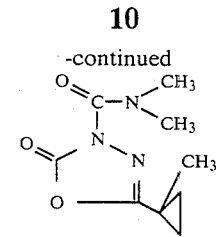

2-(1-Methylcyclopropyl)-4-Dimethylcarbamoyl-1,3,4-Δ²-Oxadiazolidin-5-one

To a stirred mixture of 10 g (0.07 mole) of 2-(1-methylcyclopropyl)-1,3,4-Δ²-oxadiazolidin-5-one (the product of Example 5) in 80 ml dimethoxyethane, 2.4 g of 60% sodium hydride (0.07 mole) were added slowly. After the reaction appeared complete, 7.5 g (0.07 mole) N,N-dimethylcarbamoyl chloride were added and the resulting mixture refluxed about 6 hours. Additional sodium hydride (about 0.5 g) was added and the mixture refluxed for about 6 hours. The reaction mixture was washed with water (300 ml) containing 1.9 g ammonium chloride) and then extracted with methylene chloride. The methylene chloride phase was dried and stripped. Chromatography on silica gel, eluting with ether, gave the product as a yellow oil.

Elemental analysis for C₉H₁₃N₃O₃ showed: calculated %C 51.18%, %H 6.2, and %N 19.9; found %C 50.76, %H 6.3, and %N 19.48.

EXAMPLE 7

Preparation of

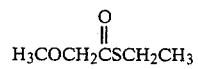

Ethyl Methoxyacetylthioate

To stirred 2-methoxyacetyl chloride, 100 g (0.92 mole), 58 g (0.92 mole) ethanethiol were added dropwise. The reaction mixture was refluxed 8 hours and then stirred over the weekend. Ether (about 300 ml) was poured in, and the resulting mixture stripped under high vacuum to give 77.5 g of product. The product was used in Example 8 without further isolation.

EXAMPLE 8

Preparation of

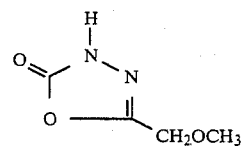

2-Methoxymethyl-1,3,4-Δ²-Oxadiazolidin-5-one

A stirred mixture of 18.50 g (0.58 mole) hydrazine and 10 ml water was cooled to 0° C.; a mixture of 77.5 g (0.58 mole) of ethyl methoxyacetylthioate (the product of Example 7) in 75 ml methanol was added dropwise. The reaction mixture was stirred overnight. The mixture was stripped and the residue dissolved in methylene chloride. The methylene chloride solution was dried with magnesium sulfate and stripped. The residue was placed in a flask with about 150 ml methylene chloride and cooled to 0° C.; 329.5 g of 12.5% phosgene (0.42 mole) were then slowly dropped in. The reaction mixture was refluxed 3½ hours and then stirred overnight. The reaction mixture was washed with water, dried over magnesium sulfate and stripped to give the above-identified product.

Elemental analysis for $C_4H_6N_2O_3$ showed: calculated %C 36.93%, %H 4.65, and %N 21.53; found %C 40.93, %H 5.28, and %N 21.17.

EXAMPLE 9

Preparation of

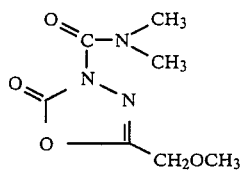

2-Methoxymethyl-4-Dimethylcarbamoyl-1,3,4-$\Delta^2$-Oxadiazolidin-5-one

To a stirred mixture of 10 g (0.077 mole) of 2-methoxymethyl-1,3,4-$\Delta^2$-oxadiazolidin-5-one (the product of Example 8) in 150 ml dimethoxyethane, 2.6 g of 60% sodium hydride were added slowly. The resulting mixture was stirred overnight. Then 8.3 g (0.077 mole) N,N-dimethylcarbamoyl chloride were added to the mixture. The resulting mixture was refluxed 5 hours. The mixture was cooled, washed with water and extracted with methylene chloride. The methylene chloride phase was dried and stripped to give the product as a yellow oil.

Elemental analysis for $C_7H_{11}N_3O_4$ showed: calculated %C 41.79%, %H 5.51, and %N 20.89; found %C 46.62, %H 6.35, and %N 19.51.

EXAMPLE 10

Preparation of

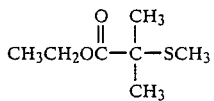

Ethyl 2-Methylthio-Isobutyrate (a) Into a solution of 52 g (0.8 mole) potassium hydroxide dissolved in 900 ml ethanol, 36.8 g methanethiol were bubbled to give a potassium mercaptide mixture which was used in Step (b).

(b) To 600 ml ethanol in a 2-liter, three-neck flask equipped with mechanical stirrer and dropping funnel with ice bath for cooling, 157.2 g (0.8 mole) ethyl 2-bromoisobutyrate were added. The mixture from Step (a) was then dropped in. The reaction mixture was stirred overnight. The reaction mixture was filtered and the filtrate stripped to give 84 g of the above-identified product.

EXAMPLE 11

Preparation of

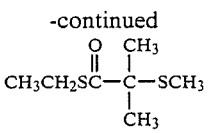

Ethyl 2-Methylthio-Isobutyrylthioate (a) To a stirred mixture of 111 g (0.68 mole) ethyl 2-methylthio-isobutyrate (the product of Example 10) and 350 ml water, 55 g of 50% sodium hydroxide (0.68 mole) were added; the resulting mixture was stirred overnight. Concentrated hydrochloric acid was added to the reaction mixture to give a pH of about 3. The reaction mixture was extracted twice with methylene chloride. The organic phase was dried and stripped to give 71 g of product which was used in Step (b) without further isolation.

(b) The product of Step (a), 71 g, was placed in a flask and stirred. After cooling to about 10° C., 63 g (0.53 mole) thionyl chloride were added slowly dropwise. The resulting mixture was refluxed 8 hours (to remove HCl gas) and then stirred overnight at ambient temperature. The reaction mixture was cooled to about 10° C.; then 33 g (0.53 mole) ethanethiol were slowly dropped in. The reaction mixture was refluxed 8 hours and then stirred overnight at ambient temperature. The product was used in Example 12 without further isolation and/or purification.

EXAMPLE 12

Preparation of

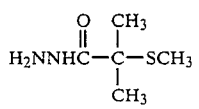

2-Methylthio-Isobutyryl Hydrazide

To a stirred mixture of 21.6 g (0.67 mole) hydrazine in 14 ml water cooled to about 0° C., 80 g (0.45 mole) ethyl 2-methylthio-isobutyrylthioate (the product of Example 11) in 250 ml methanol were slowly dropped in, maintaining the temperature of the reaction mixture at about 0° C. during the addition. The reaction mixture was stirred overnight and then stripped. Methylene chloride was added to the residue. The methylene chloride solution was dried with magnesium sulfate, filtered and stripped to give 61.3 g of the above-identified product as a black oil.

EXAMPLE 13

Preparation of

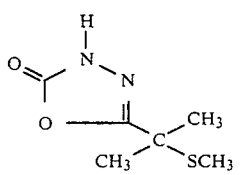

2-(2-Methylthio-Isopropyl)-1,3,4-Δ²-Oxadiazolidin-5-one

A stirred mixture of 60.5 g (0.408 mole) of 2-methylthio-isobutyryl hydrazide (the product of Example 12) was cooled to 5° C. Then 323 g of 12.5% phosgene (0.408 mole) was added dropwise. The reaction mixture was refluxed 5 hours, stirred overnight and then refluxed an additional 2 hours. The reaction mixture was cooled and then stripped. Methylene chloride (about 200 ml) was added to the residue. The resulting mixture was washed with water and the layers separated. The organic layer was dried over magnesium sulfate, filtered and stripped to give 60 g of the product as a black oil.

Elemental analysis for $C_6H_{10}N_2O_2S$ showed: calculated %C 41.36%, %H 5.78, and %N 16.08; found %C 42.88, %H 6.4, and %N 15.5.

EXAMPLE 14

Preparation of

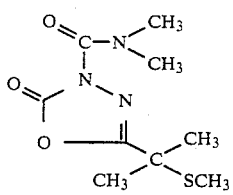

2-(2-Methylthio-Isopropyl)-4-Dimethylcarbamoyl-1,3,4-Δ²-Oxadiazolidin-5-one

To a stirred solution of 10 g (0.057 mole) 2-(2-methylthio-isopropyl-1,3,4-Δ²-oxadiazolidin-5-one (the product of Example 13) in dimethoxyethane, 2 g of 60% sodium hydride (0.057 mole) were slowly added. The reaction mixture was heated 45 minutes at about 50° C.; then 6.2 g (0.057 mole) N,N-dimethylcarbamoyl chloride were added. The resulting mixture was refluxed 3½ hours and then stirred overnight. The mixture was washed with water and then extracted with methylene chloride. The methylene chloride phase was dried, stripped and then chromatographed on silica gel, eluting with ether, to give the product as an amber oil.

Elemental analysis for $C_9H_{15}N_3O_3S$ showed: calculated %C 44.07%, %H 6.16, and %N 17.13; found %C 44.84, %H 6.53, and %N 17.44.

EXAMPLE 15

Preparation of

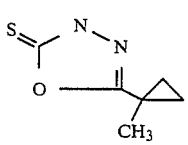

2-(1-Methylcyclopropyl)-1,3,4-Δ²-Oxadiazolidin-5-thione

To a stirred mixture of 88 g (0.77 mole) 1-methylcyclopropane carboxylic acid hydrazide in 50 ml dimethylformamide, 87.8 g (1.2 mole) carbon disulfide were added dropwise. The reaction mixture was stirred overnight and then refluxed 3 hours. The reaction mixture was filtered and then stripped to give the above-identified product as a solid, melting point 91°-93° C.

Elemental analysis for $C_6H_8N_2OS$ showed: calculated %C 46.13%, %H 5.16, and %N 17.93; found %C 46.3, %H 5.34, and %N 18.94.

EXAMPLE 16

Preparation of

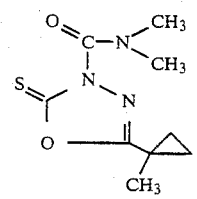

2-(1-Methylcyclopropyl)-4-Dimethylcarbamoyl-1,3,4-Δ²-Oxadiazolidin-5-thione

To a stirred mixture of 10 g (0.064 mole) 2-(1-methylcyclopropyl)-1,3,4-Δ²oxadiazolidin-5-thione (the product of Example 15) in 150 ml dimethoxyethane, 2.2 g of 60% sodium hydride were added slowly. The resulting mixture was refluxed 1 hour and then cooled. To that mixture, 6.9 g (0.064 mole) N,N-dimethylcarbamoyl chloride were added; the reaction mixture was then refluxed 3 hours. After being cooled, the reaction mixture was washed with water and extracted with methylene chloride. The methylene chloride fraction was dried over magnesium sulfate and then stripped. Chromatography on silica gel, eluting with ether, gave the product as a yellow oil.

Elemental analysis for $C_9H_{13}N_3O_2S$ showed: calculated %C 47.56%, %H 5.76, and %N 18.49; found %C 50.64, %H 6.17, and %N 19.15.

Compounds made in accordance with Examples 1 to 14 are found in Table I.

In addition, by following the procedures described in Examples 1 to 16 and using the appropriate starting materials, the following compounds are made:

2-cyclobutyl-4-dimethylcarbamoyl-1,3,4-Δ²-oxadiazolidin-5-one;

2-(1-methylcyclobutyl)-4-dimethylcarbamoyl-1,3,4-Δ²-oxadiazolidin-5-one; and 2-(1-methylcyclobutyl)-4-dimethylcarbamoyl-1,3,4-Δ²-oxadiazolidin-5-thione.

EXAMPLE A

Aphid Control

The compounds of the invention were tested for their insecticidal activity against Cotton Aphids (*Aphis gossypii* Glover). An acetone solution of the candidate toxicant containing a small amount of nonionic emulsifier was diluted with water to 40 ppm. Cucumber leaves infested with the Cotton Aphids were dipped in the toxicant solution. Mortality readings were taken after 24 hours. The results are tabulated in Table II in terms of percent control.

EXAMPLE B

Aphid Systemic Evaluation

This procedure is used to assess the ability of a candidate insecticide to be absorbed through the plant root system and translocate to the foliage.

Two cucumber plants planted in a 4-inch fiber pot with a soil surface area of 80 cm² are used. Forty ml of an 80-ppm solution of the candidate insecticide is poured around the plants in each pot. (This corresponds to 40 γ/cm² of actual toxicant.) The plants are maintained throughout in a greenhouse at 75°–85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table II in terms of percent control.

EXAMPLE C

Mite Adult

Two-spotted Mite (*Tetranychus urticae*):

An acetone solution of the candidate toxicant containing a small amount of nonionic emulsifier was diluted with water to 40 ppm. Lima bean leaves which were infested with mites were dipped in the toxicant solution. Mortality readings were taken after 24 hours. The results are tabulated in Table II in terms of percent control.

EXAMPLE D

Mite Egg Control

Compounds of this invention were tested for their ovicidal activity against eggs of the two-spotted spider mite (*Tetranychus urticae*). An acetone solution of the test toxicant containing a small amount of nonionic emulsifier was diluted with water to give a concentration of 40 ppm. Two days before testing, 2-week-old lima bean plants were infested with spider mites. Two days after infestation, leaves from the infested plants were dipped in the toxicant solution, placed in a petri dish with filter paper and allowed to dry in the open dish at room temperature. The treated leaves were then held in covered dishes at about 31° C. to 33° C. for seven days. On the eighth day, egg mortality readings were taken. The results, expressed as percent control, are tabulated in Table II.

EXAMPLE E

Housefly

Housefly (*Musca domestica* L.): A 500-ppm acetone solution of the candidate toxicant was placed in a microsprayer (atomizer). A random mixture of anesthetized male and female flies were placed in a container and 55 mg of the above-described acetone solution was sprayed on them. A lid was placed on the container. A mortality reading was made after 24 hours. The results are tabulated in Table II in terms of percent control.

EXAMPLE F

American Cockroach

American Cockroach (*Periplaneta americana* L.): A 500-ppm acetone solution of the candidate toxicant was placed in a microsprayer (atomizer). A random mixture of anesthetized male and female roaches was placed in a container and 55 mg of the above-described acetone solution was sprayed on them. A lid was placed on the container. A mortality reading was made after 24 hours. The results are tabulated in Table II in terms of percent control.

EXAMPLE G

Alfalfa Weevil

Alfalfa Weevil (*H. brunneipennis* Boheman): A 500-ppm acetone solution of the candidate toxicant was placed in a microsprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table II in terms of percent control.

EXAMPLE H

Cabbage Looper Control

The compounds of the invention were tested for their insecticidal activity against Cabbage Looper (*Trichoplusia ni*). An acetone solution of the candidate toxicant containing a small amount of nonionic emulsifier was diluted with water to 500 ppm. Excised cucumber leaves were dipped in the toxicant solution and allowed to dry. They were then infested with Cabbage Looper larvae. Mortality readings were taken after 24 hours. The results are tabulated in Table II in terms of percent control.

TABLE I

Compounds of the Formula:

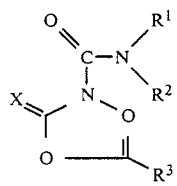

| Compound No. | | X | R¹ | R² | R³ | Physical State | ELEMENTAL ANALYSIS | | | | | |
|---|---|---|---|---|---|---|---|---|---|---|---|---|
| | | | | | | | % Carbon | | % Hydrogen | | % Nitrogen | |
| | | | | | | | Calc. | Found | Calc. | Found | Calc. | Found |
| 1 | 33157 | O | CH₃ | CH₃ | CH₃ | Tan Solid, m.p. 58–61° C. | 42.1 | 42.28 | 5.3 | 5.58 | 24.55 | 24.24 |
| 2 | 33047 | O | CH₃ | CH₃ | C(CH₃)₃ | White Solid, m.p. 71–73° C. | 50.69 | 50.89 | 7.09 | 7.24 | 19.71 | 20.11 |

TABLE I-continued

Compounds of the Formula:

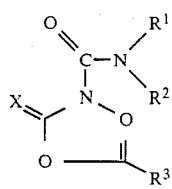

| Compound No. | X | R¹ | R² | R³ | Physical State | % Carbon Calc. | % Carbon Found | % Hydrogen Calc. | % Hydrogen Found | % Nitrogen Calc. | % Nitrogen Found |
|---|---|---|---|---|---|---|---|---|---|---|---|
| 3  33286 | O | CH₃ | CH₃ | cyclopropyl | White Solid, m.p. 62–64° C. | 48.73 | 48.64 | 5.62 | 5.87 | 21.31 | 20.93 |
| 4  34332 | O | CH₃ | CH₃ | 1-methylcyclopropyl | Yellow Oil | 51.18 | 50.76 | 6.2 | 6.3 | 19.9 | 19.48 |
| 5  33904 | O | CH₃ | CH₃ | cyclopentyl | Yellow Oil | 53.32 | 54.5 | 6.71 | 6.93 | 18.66 | 18.0 |
| 6  33557 | O | CH₃ | CH₃ | cyclohexyl | Yellow Oil | 55.22 | 54.61 | 7.16 | 7.09 | 17.56 | 16.75 |
| 7  34333 | O | CH₃ | CH₃ | 1-methylcyclohexyl | Yellow Oil | 56.9 | 56.91 | 7.56 | 7.61 | 16.59 | 16.13 |
| 8  35139 | S | CH₃ | CH₃ | 1-methylcyclopropyl | Yellow Oil | 47.56 | 50.64 | 5.76 | 6.17 | 18.49 | 19.15 |
| 9  35682 | S | CH₃ | CH₃ | 1-methylcyclohexyl | Yellow Oil | 53.51 | 52.34 | 7.11 | 7.24 | 15.6 | 15.92 |
| 10 34019 | O | CH₃ | CH₃ | —CH₂OCH₃ | Yellow Oil | 41.8 | 46.6 | 5.51 | 6.35 | 20.89 | 19.51 |
| 11 34246 | O | CH₃ | CH₃ | —C(CH₃)₂SCH₃ | Amber Oil | 44.07 | 44.84 | 6.16 | 6.53 | 17.13 | 17.44 |

TABLE II

| Compound No. | A | AS | MA | ME | HF | AR | AW | CL |
|---|---|---|---|---|---|---|---|---|
| 1  33157 | 90 | 0 | 0 | 0 | 15 | 0 | 30 | 0 |
| 2  33047 | 100 | 100 | 0 | 0 | 100 | 100 | 90 | 10 |
| 3  33286 | 96 | 0 | 0 | 0 | 78 | 39 | 0 | 0 |
| 4  34332 | 100 | 0 | 0 | 0 | 99 | 100 | 50 | 0 |
| 5  33904 | — | 0 | 0 | 0 | 75 | 78 | 10 | 30 |
| 6  33557 | 96 | 0 | 0 | 0 | 0 | 0 | 0 | 0 |
| 7  34333 | 100 | 100 | 0 | 0 | 0 | 100 | 30 | 0 |
| 8  35139 | 90 | 0 | 0 | 0 | 0 | 0 | 0 | 0 |
| 9  35682 | 78 | 0 | 0 | 96 | 0 | 0 | 0 | 0 |
| 10 34019 | 100 | 0 | 0 | 0 | 94 | 10 | 0 | 0 |
| 11 34246 | 100 | 100 | 94 | 0 | 99 | 100 | 90 | 20 |

A = Aphid
AS = Aphid Systemic
MA = Mite Adult
ME = Mite Egg
HF = Housefly
AR = American Cockroach
AW = Alfalfa Weevil
CL = Cabbage Looper

What is claimed is:

1. A compound of the formula:

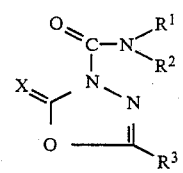

wherein X is oxygen or sulfur, R¹ and R² are independently lower alkyl having from 1 to 4 carbon atoms; and R³ is lower cycloalkyl having from 3 to 6 carbon atoms substituted with methyl or ethyl, lower alkoxyalkyl having up to a total of 8 carbon atoms or lower alkylthioalkyl having up to a total of 8 carbon atoms.

2. A compound according to claim 1 wherein R¹ and R² are methyl.

3. A compound according to claim 2 wherein X is oxygen.

4. A compound according to claim 1 wherein $R^3$ is lower alkoxyalkyl or lower alkylthioalkyl.

5. A compound according to claim 1 wherein $R^3$ is a tertiary carbon of the formula:

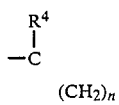

wherein $R^4$ is methyl or ethyl and n is an integer between 2 and 5.

6. A compound according to claim 3 wherein $R^3$ is

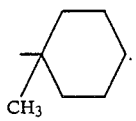

7. A compound according to claim 3 wherein $R^3$ is $-C(CH_3)_2SCH_3$.

8. A method for killing insects which comprises contacting said insects or their habitat with an insecticidally effective amount of the compound of the formula defined in claim 1.

9. A method for killing insects which comprises contacting said insects or their habitat with an insecticidally effective amount of the compound of the formula defined in claim 4.

10. A method for killing insects which comprises contacting said insects or their habitat with an insecticidally effective amount of the compound of the formula defined in claim 5.

11. A method for killing insects which comprises contacting said insects or their habitat with an insecticidally effective amount of the compound of the formula defined in claim 2.

12. A method for killing insects which comprises contacting said insects or their habitat with an insecticidally effective amount of the compound of the formula defined in claim 6.

13. A method for killing insects which comprises contacting said insects or their habitat with an insecticidally effective amount of the compound of the formula defined in claim 7.

14. An insecticidal composition comprising a biologically inert carrier and an insecticidally effective amount of a compound of the formula defined in claim 1.

15. An insecticidal composition comprising a biologically inert carrier and an insecticidally effective amount of a compound of the formula defined in claim 4.

16. An insecticidal composition comprising a biologically inert carrier and an insecticidally effective amount of a compound of the formula defined in claim 5.

17. An insecticidal composition comprising a biologically inert carrier and an insecticidally effective amount of a compound of the formula defined in claim 2.

18. An insecticidal composition comprising a biologically inert carrier and an insecticidally effective amount of a compound of the formula defined in claim 6.

19. An insecticidal composition comprising a biologically inert carrier and an insecticidally effective amount of a compound of the formula defined in claim 7.

* * * * *